United States Patent [19]

Umezawa et al.

[11] Patent Number: 4,469,683
[45] Date of Patent: Sep. 4, 1984

[54] 3''-EPISTREPTOMYCIN AND ITS DIHYDRO DERIVATIVE, PHARMACEUTICAL COMPOSITIONS AND PRODUCTION OF THE SAME

[75] Inventors: Hamao Umezawa; Sumio Umezawa, both of Tokyo; Tsutomu Tsuchiya, Yokohama; Tetsuo Shitara, Tokyo; Shuichi Sakamoto, Kodaira, all of Japan

[73] Assignee: Zaidan Hojin Biseibutsu Kagaku Kenkyu Kai, Tokyo, Japan

[21] Appl. No.: 473,921

[22] Filed: Mar. 10, 1983

[30] Foreign Application Priority Data

Mar. 10, 1982 [JP] Japan ................... 57-36523

[51] Int. Cl.$^3$ ..................... A61K 31/71; C07H 15/22
[52] U.S. Cl. ..................... 424/180; 536/14; 536/15; 536/16
[58] Field of Search ..................... 536/14, 15, 16, 13.6; 424/180

[56] References Cited

U.S. PATENT DOCUMENTS 2,663,685 12/1953 Levy ....................... 536/15
2,790,792 4/1957 Kaplan .................... 536/15
2,857,375 10/1958 Ziegler ................... 536/16
4,171,356 10/1979 Wright et al. ............ 536/13.6

Primary Examiner—Johnnie R. Brown
Attorney, Agent, or Firm—Sughrue, Mion, Zinn, Macpeak and Seas

[57] ABSTRACT

New semi-synthetic antibiotics, 3''-epistreptomycin and 3''-epidihydrostreptomycin are now provided, which are useful as antibacterial agents. 3''-Epidihydrostreptomycin is produced by a process comprising hydrolyzing an appropriately N,O-protected 2'',3''-N,O-carbonyl-3''-epidihydrostreptomycin which is prepared by skilled introduction of amino-protecting groups and hydroxyl-protecting groups of appropriately selected natures into dihydrostreptomycin and intermolecular condensation of a particular pair of amino-protecting and hydroxyl-protecting groups so introduced. 3''-Epistreptomycin is produced by a process comprising oxidizing the 3'-hydroxymethyl group of an appropriately N,O-protected 3''-epidihydrostreptomycin as prepared by skilled introduction of amino-protecting groups and hydroxyl-protecting groups of appropriately selected natures, and then removing the remaining protective groups from the resultant N,O-protected 3''-epistreptomycin obtained as the oxidation product.

10 Claims, No Drawings

3''-EPISTREPTOMYCIN AND ITS DIHYDRO DERIVATIVE, PHARMACEUTICAL COMPOSITIONS AND PRODUCTION OF THE SAME

SUMMARY OF THE INVENTION

This invention relates to new streptomycin derivatives which are new substances and useful as antibacterial agents. More particularly, this invention relates to 3''-epistreptomycin and 3''-epidihydrostreptomycin and also to processes for the production of these new streptomycin derivatives.

BACKGROUND OF THE INVENTION

Streptomycin is a well known antibiotic which was discovered by Wasksman. Streptomycin, and dihydrostreptomycin which is obtained by reduction of the aldehyde group of streptomycin are widely used as medicine in therapeutic treatment of bacterial infections. However, as streptomycin and dihydrostreptomycin become widely used, such strains of bacteria resistant to these antibiotics have occurred, and owing to this the therapeutic effects of streptomycin and dihydrostreptomycin have considerably been reduced. The occurrence of such resistant bacteria is generally observed not only with the antibiotics of streptomycin type but also with other antibiotics such as kanamycins, lividomycins and the like. These historical facts are detailed in the general remarks as reported by Hamao Umezawa who is one of the present inventors and is a first discoverer of the mechanism of resistance of bacteria against aminoglycosidic antibiotics (H. Umezawa; "Advances in Carbohydrate Chemistry and Biochemistry" Vol. 30, page 183, Academic Press 1974). With the streptomycins, it has been found that the hydroxyl group at 3''-position of the molecule of streptomycins can be adenylated by such resistant bacteria capable of producing streptomycin adenyl-transferase and thereby 3''-O-adenylstreptomycins are formed, with a consequence that streptomycins can be inactivated in respect of their antibacterial effects (Umezawa et al.; "Journal of Antibiotics" Vol. 21, page 81 (1968)). In these circumstances, we, the present inventors, have conducted studies in an attempt to remove the 3''-hydroxyl group from the streptomycin molecule and thereby to eliminate the possibility of inactivation of streptomycin which would occur due to the adenylation of the 3''-hydroxyl group of streptomycin, so that there was provided a new derivative of streptomycin which would be active also against the bacteria resistant to streptomycin. As a result of our study, we succeeded in synthesizing 3''-deoxydihydrostreptomycin from streptomycin, and we found that this 3''-deoxydihydrostreptomycin is active against the resistant bacteria (see Japanese patent application prepublication "Kokai" No. 105154/77; and "Journal of Antibiotics" Vol. 29, page 978 (1976)).

We have made our further study and have now succeeded in effecting the epimerization of the 3''-hydroxyl group of streptomycin and dihydrostreptomycin, and we have now found that the 3''-epistreptomycin and 3''-epidihydrostreptomycin now newly synthesized are active against a variety of streptomycin-resistant bacteria. Thus, we have accomplished this invention.

DETAILED DESCRIPTION OF THE INVENTION

According to a first embodiment of this invention, therefore, there are provided as new compounds a 3''-epistreptomycin compound represented by the general formula

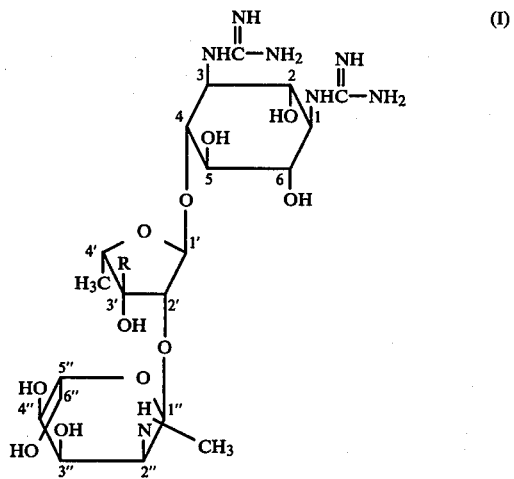

wherein R denotes a hydroxymethyl group—$CH_2OH$ for 3''-epidihydrostreptomycin and R denotes an aldehyde group —CHO for 3''-epistreptomycin, and a pharmaceutically acceptable acid-addition salt thereof.

The pharmaceutically acceptable acid-addition salt of the new compound of the above general formula (I) includes a salt of 3''-epistreptomycin or 3''-epidihydrostreptomycin with an ordinary, non-toxic acid such as an inorganic acid, for example, hydrochloric acid, sulfuric acid, phosphoric acid and the like, as well as an organic acid, for example, acetic acid, malonic acid, citric acid and the like.

3''-Epistreptomycin tri-hydrochloride mono-hydrate according to this invention is in the form of a colorless, solid substance which shows a specific optical rotation $[\alpha]_D^{23} - 80°$ (c 1, water) but shows no definite melting point. Its elemental analysis (Found: C 35.22, H 6.51, N 13.58%) was coincident with the theoretical value of the empirical formula $C_{21}H_{39}N_7O_{12} \cdot 3HCl \cdot H_2O$ (Calculated: C 35.58, H 6.26, N 13.83%).

3''-Epidihydrostreptomycin 3/2 carbonate according to this invention is in the form of a colorless, solid substance which shows a specific optical rotation $[\alpha]_D^{23} - 79°$ (c 0.9, water) but shows no definite melting point. Its elemental analysis (Found: C 39.63, H 6.47, N 14.33%) was coincident with the theoretical value of the empirical formula $(C_{21}H_{41}N_7O_{12} \cdot 3/2H_2CO_3)$ (Calculated: C 39.94, H 6.55, N 14.49%).

The antibacterial activities of 3''-epistreptomycin and 3''-epidihydrostreptomycin are demonstrated in Table 1 below, which exhibits the minimum inhibitory concentrations (mcg/ml) of the new compounds of this invention as estimated according to a standard serial dilution method using a nutrient agar medium as the incubation medium, the incubation being made at 37° C. for 17 hours. Minimum inhibitory concentrations (mcg/ml) of streptomycin and dihydrostreptomycin were also estimated in the same manner as above for the comparison purpose and are shown in Table 1 below. As shown in Table 1, the new compounds of the formula (I) according to this invention exhibit antibacterial spectra similar to those of the comparative dihydrostreptomycin and show remarkably improved antibacterial activities against gram-negative bacteria, especially against various resistant strains of *Escherichia coli*.

TABLE 1

|  | MIC (mcg/ml) | | | |
| --- | --- | --- | --- | --- |
| Test organism | 3''-Epidihydro-streptomycin | 3''-Epi-streptomycin | Dihydro-streptomycin (comparative) | Streptomycin (comparative) |
| *Staphylococcus aureus* 209P | 3.12 | 3.12 | 3.12 | 3.12 |
| *Staphylococcus aureus* AP01 | 3.12 | 3.12 | 1.56 | 3.12 |
| *Sarcia lutea* PCI 1001 | 1.56 | 3.12 | 1.56 | 1.56 |
| *Bacillus subtilis* NRRL B558 | 3.12 | 1.56 | 3.12 | 0.78 |
| *Salmonella typhi* T-63 | 0.78 | 1.56 | 25 | 25 |
| *Escherichia coli* K-12 | 1.56 | 1.56 | 1.56 | 1.56 |
| *Escherichia coli* K-12 R5 | 6.25 | 6.25 | >100 | >100 |
| *Escherichia coli* K-12 ML1629 | 1.56 | 3.12 | 100 | >100 |
| *Escherichia coli* K-12 ML1630 | 3.12 | 3.12 | >100 | >100 |
| *Escherichia coli* K-12 ML1630 R8125 | 25 | 25 | >100 | >100 |
| *Escherichia coli* W677 | 1.56 | 1.56 | 0.78 | 1.56 |
| *Escherichia coli* JR66/W677 | 12.5 | 12.5 | >100 | >100 |
| *Escherichia coli* C600 R135 | 3.12 | 3.12 | 50 | 50 |
| Providencia sp. pv16 | 6.25 | 3.12 | 25 | 25 |
| *Pseudomonas aeruginosa* 33 | 3.12 | 6.25 | 1.56 | 3.12 |
| *Pseudomonas aeruginosa* No. 12 | 25 | 25 | 25 | 25 |
| *Pseudomonas aeruginosa* 13—13 | 50 | 50 | >100 | >100 |
| *Mycobacterium smegmatis* 607 | 0.78 | 1.56 | 0.78 | 0.78 |

The new compounds of this invention, namely 3''-epistreptomycin and 3''-epidihydrostreptomycin can be administered to living animals, including men, safely as much as the known streptomycin and dihydrostreptomycin for therapeutical treatment of bacterial infections, because they are of low toxicity as will be shown by the fact that when acute toxicity of 3''-epistreptomycin or 3''-epidihydrostreptomycin was estimated by intravenous injection of these compounds in groups of mice (ICR mice, adult, female, body weight 20 g.±0.5 g. six in each group), all the treated mice survived for more than 14 days after the new compound of this invention was administered intravenously into each mouse at a dosage of 4 mg/kg (LD$_{50}$ more than 200 mg/kg).

Processes for the production of the new compounds of the formula (I) according to this invention are described in the following.

Briefly, 3''-epidihydrostreptomycin of this invention is produced starting from the known dihydrostreptomycin, and 3''-epistreptomycin of this invention is produced form the 3''-epidihydrostreptomycin now newly synthetized.

Firstly, a summary of a process for the production of 3''-epidihydrostreptomycin is illustrated by the following first flow diagram which shows the production of 3''-epidihydrostreptomycin from dihydrostreptomycin via about eight stages. In the first flow diagram and also in the another flow diagrams shown later, such intermolecular sites of the compound which just have undergone chemical change or modification through the chemical reaction at a particular stage of the concerned process are preferentially represented in the respective flow diagrams, so that such substituent or substituents which is or are existing in the compound in one particular stage but is or are remaining unchanged in the compound in the next stage (that is, the stage just following said particular stage) are sometimes omitted from being shown in the next stage of the flow diagram, for sake of simplicity. In the following flow diagrams, Ac denotes an acetyl group.

First Flow Diagram

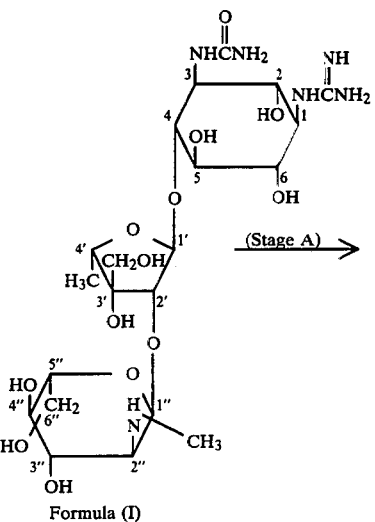

Formula (I)

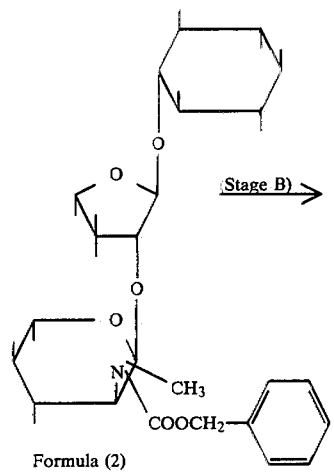

Formula (2)

-continued
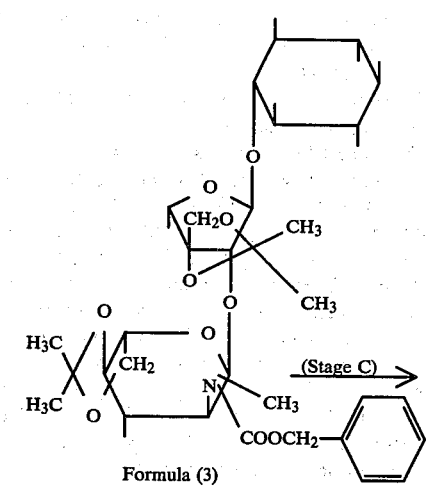
Formula (3)
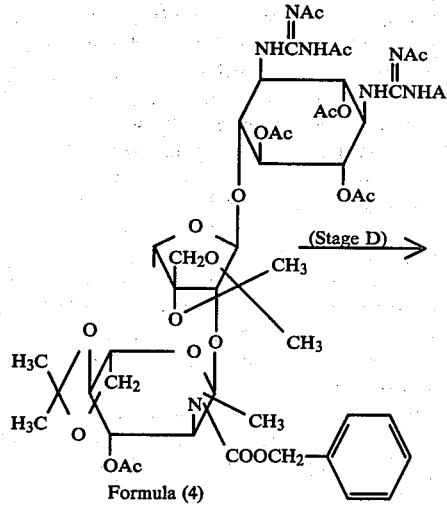
Formula (4)
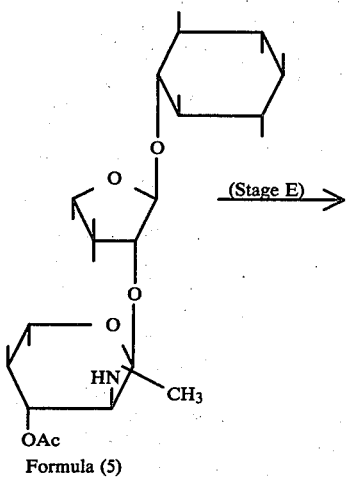
Formula (5)
-continued
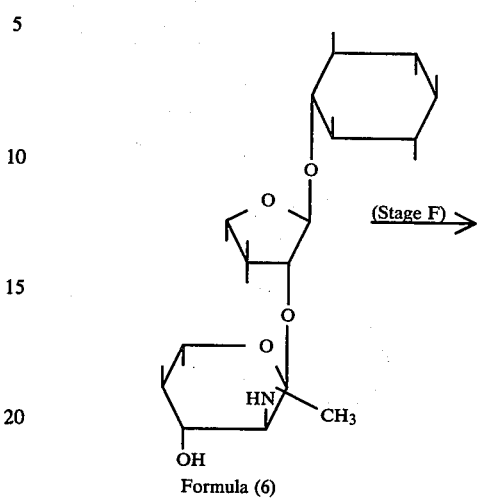
Formula (6)
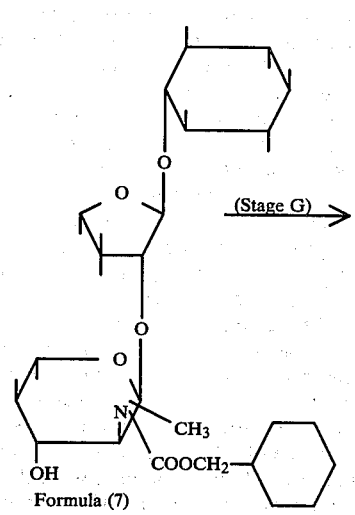
Formula (7)
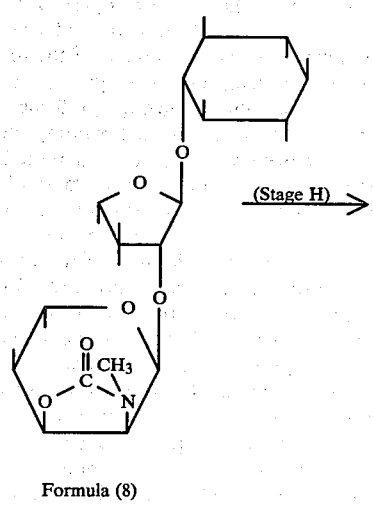
Formula (8)

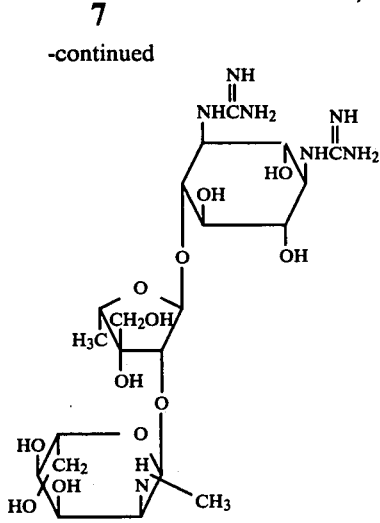

Formula (I′)

Now, a process of producing 3″-epidihydrostreptomycin is described with reference to the respective stages of the process shown in the first flow diagram as above and is fully illustrated by Example 1 given later.

Dihydrostreptomycin which is used as the starting substance in this process is the compound represented by the formula (1) in the first flow diagram. To synthetize 3″-epidihydrostreptomycin of this invention with starting from dihydrostreptomycin, at first, the 2″-methylamino group of the compound of the formula (1) is selectively protected in Stage A of the process by a known aminoprotecting group such as an aralkyloxycarbonyl group, preferably benzyloxycarbonyl group. To this end, the starting compound of the formula (1) may preferably be reacted with a 1 molar or substantially 1 molar proportion of benzyloxycarbonyl chloride in a mixture of water and acetone at a temperature of −20° C. to 50° C., preferably at 0° C. under ice-cooling in the presence of a base, preferably an alkali metal carbonate such as sodium carbonate, whereby the preferential benzyloxycarbonylation of the 2″-methylamino group takes place to produce 2″-N-benzyloxycarbonyl-dihydrostreptomycin briefly represented by the formula (2) in the first flow diagram.

Then, in Stage B of this process, a pair of two 3′- and 3′a-hydroxyl groups as well as a pair of two 4″- and 6″-hydroxyl groups of the compound of the formula (2) are protected by a known di-valent hydroxyl-protecting group such as an alkylidene group, preferably isopropylidene group. For this purpose, the compound of the formula (2) may preferably be reacted with 2,2-dimethoxypropane in anhydrous dimethylformamide (DMF) in the presence of a reaction catalyst such as p-toluenesulfonic acid, whereby the pair of the two 3′- and 3′a-hydroxyl groups as well as the pair of the two 4″- and 6″-hydroxyl groups of the compound of the formula (2) are each protected simultaneously by a single isopropylidene group, to afford 2″-N-benzyloxycarbonyl-3′,3′a; 4″,6″-di-O-isopropylidene-dihydrostreptomycin briefly represented by the formula (3) in the first flow diagram.

Thereafter, in Stage C of this process, all the remaining free (four) hydroxyl groups and all the two guanidyl groups of the compound of the formula (3) are protected, respectively. To this end, all these functional hydroxyl and guanidyl groups may preferably be blocked by acetyl groups. The acetylation reagent available for this purpose may be acetic anhydride as used in the presence of sodium acetate. Thus, the compound of the formula (3) is reacted with acetic anhydride in the presence of sodium acetate using an excess of acetic anhydride as the reaction medium, when there is produced tetra-N-$^G$-acetyl-2,5,6,3″-tetra-O-acetyl-2″-N-benzyloxycarbonyl-3′,3′a; 4″, 6″-di-O-isopropylidene-dihydrostreptomycin represented by the formula (4) in the first flow diagram.

Further, in Stage D of this process, the compound of the formula (4) is treated so as to remove preferentially the 2″-N-benzyloxycarbonyl group therefrom and thereby liberate the free 2″-methylamino group. For this purpose, the compound of the formula (4) may preferably be subjected to catalytic hydrogenolysis with hydrogen in the presence of a known hydrogenolysis catalyst such as palladium black as be conducted conventionally in the deprotection technique for removal of the amino-protecting benzyloxycarbonyl group. There is thus formed tetra-$N^G$-acetyl-2,5,6,3″-tetra-O-acetyl-3′,3′a; 4″,6″-di-O-isopropylidene-dihydrostreptomycin briefly represented by the formula (5) in the first flow diagram.

Moreover, in Stage E of the present process, the compound of the formula (5) is treated so as to remove preferentially the blocking acetyl group from the 3″-hydroxyl group of the compound (5). For this purpose, the compound (5) is dissolved in a volume of ethanol, and the resulting ethanolic solution is allowed to stand at a temperature of 20°–30° C. for 1 day or usually for a period of about 3 days, whereby the selective removal of the 3″-O-acetyl group takes place through the ethanolysis. This unique fact that the blocking acetyl group can be removed only from the 3″-hydroxyl group of the compound (5) while the other blocking O-acetyl groups are not cleaved out of the 2-, 5- and 6-hydroxyl groups of said compound is unexpected and surprising. Through this Stage E, there is formed tetra-$N^G$-acetyl-2,5,6-tri-O-acetyl-3′,3′a; 4″,6″-di-O-isopropylidenedihydrostreptomycin briefly represented by the formula (6) in the first flow diagram.

Then, in Stage F of the present process, the 2″-methylamino group of the compound of the formula (6) is again protected by a benzyloxycarbonyl group. To this end, the compound of the formula (6) may either be reacted with benzyloxycarbonyl chloride in the same manner as in the aforesaid Stage A, or may be reacted with benzyloxycarbonyl chloride in chloroform in the presence of sodium hydrogen carbonate. In this way, there is produced tetra-$N^G$-acetyl-2,5,6-tri-O-acetyl-2″-N-benzyloxycarbonyl-3′,3′a; 4″,6″-di-O-isopropylidenedihydrostreptomycin birefly represented by the formula (7) in the first flow diagram.

Thereafter, in Stage G of the present process, the compound of the formula (7) is dissolved into a volume of a suitable organic solvent such as dichloromethane and the resultant solution of the compound (7) is reacted with a 1–10 molar proportion of trifluoromethanesulfonic acid anhydride in the presence of pyridine under cooling (preferably at a temperature of approximately −50° C. ∼ +50° C.), so that there is once formed an unstable 3″-O-trifluoromethylsulfonyl derivative of the compound (7) as a glassy material. This glassy material is then dissolved into a volume of pyridine and allowed to stand at a temperature of 10° C. ∼ 100° C., preferably at ambient temperature, when the 3″-trifluoromethylsulfonyl group is interacted and condensed with the 2″-benzyloxycarbonylmethylamino group, so that the cyclisation reaction takes place to form a cyclic carbamate group, giving the compound of the formula (8) briefly shown in the first flow diagram, namely tetra-$N^G$-acetyl-2,5,6-tri-O-acetyl-2″,3″-N,O-carbonyl-3″-epi-3′,3′a; 4″,6″-di-O-isopropylidenedihydrostreptomycin.

Finally, in Stage H of the present process, the compound of the formula (8) is subjected to an N,O-deprotecting treatments as well as removal of the 2″,3″-N,O-carbonyl group by a hydrolytic ring-fission thereof. That is, the removal of the N,O-protecting acetyl groups and the removal of the cyclic carbamate group (the 2″,3″-N,O-carbonyl group) from the compound of the formula (8) are effected in this Stage H. For this purpose, the compound of the formula (8) may conveniently by hydrolyzed in aqueous tetrahydrofuran in the presence of barium hydroxide, so that both of the acetyl groups and the cyclic carbamate group can be removed at once. The liberated 3″-hydroxyl group which has undergone the decarbonylation just at this stage of removal of the 2″,3″-N,O-carbonyl group is remaining inversed in the epi-position, so that there is formed 3″-epi-3′,3′a; 4″,6″-di-O-isopropylidenedihydrostreptomycin. The latter compound is further necessary in this Stage H to be subjected to removal of the 3′,3′a; 4″,6″-di-O-isopropylidene groups therefrom, and this can be achieved according to a conventional method for removing the isopropylidene group known in the usual deprotection technique. For instance, the removal of the 3′,3′a; 4″,6″-di-O-isopropylidene groups may be accomplished by hydrolyzing the intermediate 3″-epi-3′,3′a; 4″,6″-di-O-isopropylidenedihydrostreptomycin in aqueous acetic acid. In this way, there is produced the aimed 3″-epidihydrostreptomycin, represented by the formula (I′) in the first flow diagram.

In the foregoing descriptions, the process of producing the compound of the formula (I′) of this invention is described with reference to such a case where the benzyloxycarbonyl group, isopropylidene group and acetyl group are particularly selected as the protective groups. It will be self-evident, however, that the required, N,O-protection of the concerned compounds can be achieved using such a known amino-protecting group which serves equivalently to the benzyloxycarbonyl group; and such a known guanidyl-amino (or imino) protecting group which serves equivalently to the acetyl group, as well as such known hydroxyl-protecting groups which serve equivalently to the isopropylidene group and acetyl group, respectively.

According to a second embodiment of this invention, therefore, there is provided a process for the production of 3″-epidihydrostreptomycin, which comprises the consecutive steps of:

(a) Reacting tetra-$N^G$-acetyl-2,5,6,3″-tetra-O-acetyl-3′,3′a; 4″, 6″-di-O-isopropylidene-dihydrostreptomycin of the formula

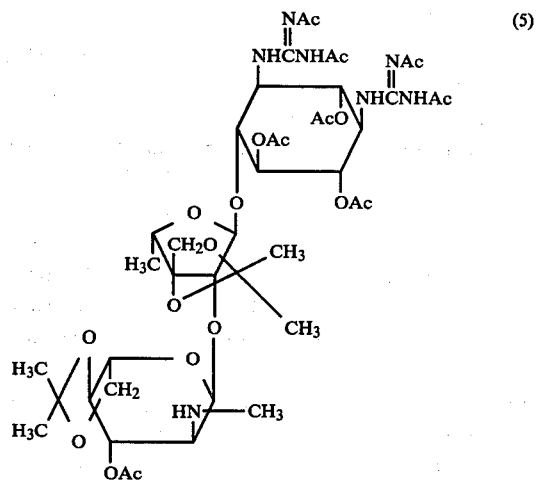

wherein Ac denotes an acetyl group, with ethanol at a temperature of 20°–30° C. to effect preferential removal of the 3″-O-acetyl group from the above N,O-protected dihydrostreptomycin compound and thereby to produce tetra-$N^G$-acetyl-2,5,6-tri-O-acetyl-3′,3′a; 4″, 6″-O-isopropylidenedihydrostreptomycin, (b) Reacting the product of the step (a) just above with benzyloxycarbonyl chloride to produce tetra-$N^G$-acetyl-2,5,6-tri-O-acetyl-2″-N-benzyloxycarbonyl-3′,3′a; 4″,6″-di-O-isopropylidene-dihydrostreptomycin, (c) Reacting the product of the step (b) just above with trifluoromethanesulfonic acid anhydride in pyridine at a temperature of −50° C. to 50° C. to form the 30″-O-trifluoromethylsulfonyl derivative thereof, followed by allowing the latter derivative to stand in solution in pyridine at a temperature of 10° C. to 100° C. to produce tetra-$N^G$-acetyl-2,5,6-tri-O-acetyl-2″,3″-N,O-carbonyl-3″-epi-3′,3′a; 4″,6″-di-O-isopropylidene-dihydrostreptomycin of the formula

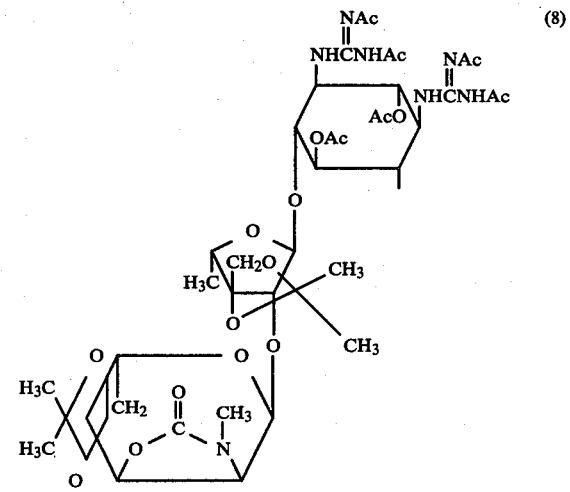

wherein Ac is as defined as above.

(d) Hydrolyzing the product of the step (c) just above with water in the presence of barium hydroxide to remove all the acetyl groups and the 2″,3″-N,O-carbonyl group therefrom and thus to produce 3″-epi-3′,3′a; 4″,6″-di-O-isopropylidene-dihydrostreptomycin, and (e) Hydrolyzing the product of the step (d) just above to remove the 3',3'a; 4",6"-di-O-isopropylidene groups therefrom and thus to produce the desired 3"-epidihydrostreptomycin.

Besides, the second new compound of this invention, namely 3"-epistreptomycin can be produced with starting from the 3"-epidihydrostreptomycin now newly synthetized as above. A summary of such a process of producing 3"-epistreptomycin is illustrated by the following second flow diagram, where such intermolecular sites of the compound which just have undergone chemical change or modification through the chemical reaction at one particular stage of the process concerned are preferentially represented, so that such substituent or substituents which is or are existing in the concerned compound in one particular stage but is or are remaining unchanged in the next stage following said particular stage are sometimes omitted from being shown in the next stage of the second flow diagram, for sake of simplicity.

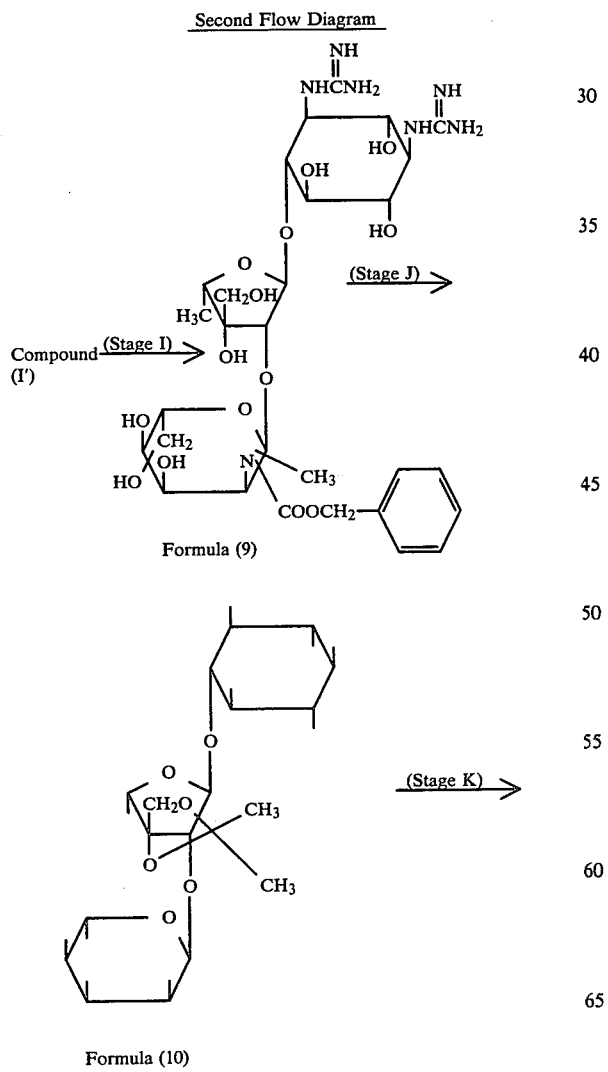

Second Flow Diagram

Formula (9)

Formula (10)

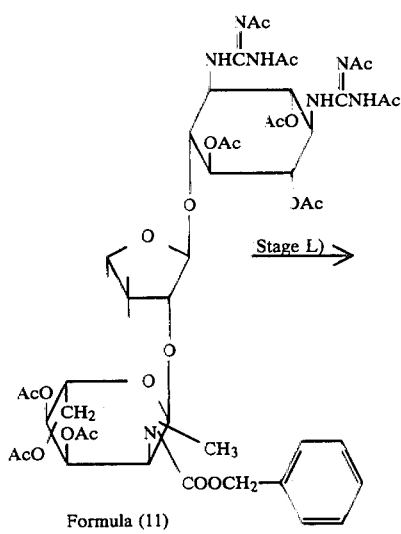

Formula (11)

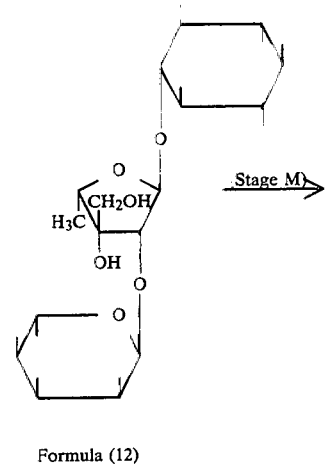

Formula (12)

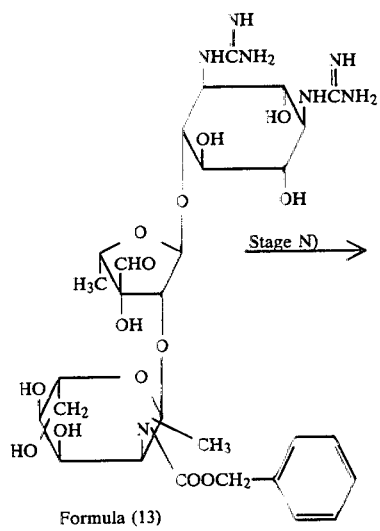

Formula (13)

-continued

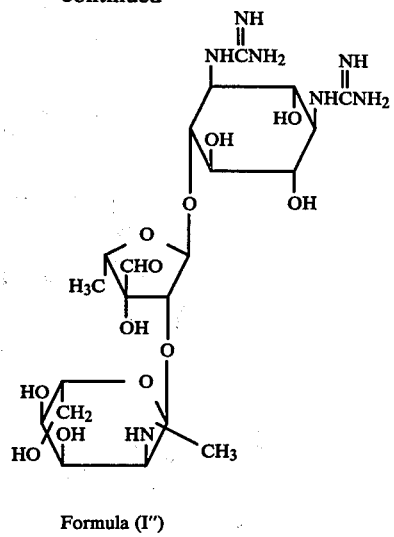

Formula (I″)

In the following, a process of producing 3″-epistreptomycin from 3″-epidihydrostreptomycin is described with reference to the respective stages of the process shown in the second flow diagram as above and is fully illustrated by Example 2 given later.

3″-Epidihydrostreptomycin which is employed as the starting substance in this process is the compound of the formula (I′) shown in the first flow diagram given hereinbefore. In Stage I of this process, the 2″-methylamino group of the starting compound of the formula (I′) is at first protected preferentially with benzyloxycarbonyl group by reacting the starting compound (I′) with benzyloxycarbonyl chloride in the same manner as in Stage A of the process according to the first flow diagram. There is thus formed 2″-N-benzyloxycarbonyl-3″-epidihydrostreptomycin of the formula (9) shown in the second flow diagram, which is usually obtained in the form of its hydrochloride.

In Stage J of this process, a pair of two 3′- and 3′a-hydroxyl groups of the compound of the formula (9) is protected with a known di-valent hydroxyl-protecting group such as an alkylidene group. To this end, the compound of the formula (9) may be reacted with an excess over the 1 molar proportion of 2,2-dimethoxypropane in anhydrous DMF in the presence of p-toluenesulfonic acid, so that the desired mono-O-isopropylidenated product is formed in mixture with some poly-O-isopropylidenated products. The poly-O-isopropylidenated products can be converted into the desired mono-O-isopropylidenated product by treatment with aqueous acetic acid. There is thus produced 2″-N-benzyloxycarbonyl-3″-epi-3′,3′a-O-isopropylidenedihydrostreptomycin of the formula (10) briefly shown in the second flow diagram.

In the next stage K of this process, all the remaining free hydroxyl groups and all the guanidyl groups of the compound of the formula (10) are protected with suitable protective groups. For this purpose, the compound of the formula (10) may preferably be acetylated in the same manner as in Stage C of the process according to the first flow diagram, that is, by reacting with a 10 molar proportion or more of acetic anhydride in the presence of sodium acetate. By this Stage K, there is produced tetra-$N^G$-acetyl-2,5,6,3″,4″,6″-hexa-O-acetyl-2″-N-benzyloxycarbonyl-3″-epi-3′,3′a-O-iso-propylidenedihydrostreptomycin of the formula (11) briefly shown in the second flow diagram.

In Stage L of this process, the compound of the formula (11) is then subjected to removal of the 3′,3′a-O-isopropylidene group therefrom in the same manner as in Stage H of the process according to the first flow diagram, by hydrolyzing the compound (11) in aqueous acetic acid, so that there is produced the compound of the formula (12) briefly shown in the second flow diagram, namely tetra-$N^G$-acetyl-2,5,6,3″,4″,6″-hexa-O-acetyl-2″-N-benzyloxycarbonyl-3″-epidihydrostreptomycin.

Next, in Stage M of the present process, the 3′-hydroxymethyl group (the methylol group) of the compound of the formula (12) is oxidized into the aldehyde group —CHO. To this end, the compound of the formula (12) may preferably be reacted with dimethylsulfoxide as an oxidation reagent in the presence of pyridine, trifluoroacetic acid and dicyclohexylcarbodiimide. There is thus produced tetra-$N^G$-acetyl-2,5,6,3″,4″,6″-hexa-O-acetyl-2″-N-benzyloxycarbonyl-3″-epistreptomycin (which is not shown in the second flow diagram). The latter aldehyde compound is then subjected to removal of the acetyl groups therefrom, and this deacetylation may conveniently be effected by hydrolysing said aldehyde compound with concentrated aqueous ammonia in methanol. In this way, there is produced 2″-N-benzyloxycarbonyl-3″-epistreptomycin of the formula (13) shown in the second diagram.

After the above deacetylation step, in the final Stage N of the present process, the compound of the formula (13) is subjected to removal of the 2″-N-benzyloxycarbonyl group therefrom to give the desired 3″-epistreptomycin of the formula (I″) shown in the second diagram. To remove the 2″-N-benzyloxycarbonyl group from the compound (13), the latter compound may conveniently be subjected to a conventional catalytic hydrogenolysis with hydrogen in the presence of a known hydrogenolysis catalyst such as palladium black according to the known deprotection technique.

According to a third embodiment of this invention, therefore, there is provided a process for the production of 3″-epistreptomycin which comprises the consecutive steps of:

(a) Reacting 3″-epidihydrostreptomycin with a 1 molar or substantially 1 molar proportion of benzyloxycarbonyl chloride in a mixture of water and acetone at a temperature of −20° C. to 50° C. in the presence of an alkali metal carbonate to selectively benzyloxycarbonylate the 2″-methylamino group of 3″-epidihydrostreptomycin and thereby to produce 2″-N-benzyloxycarbonyl-3″-epidihydrostreptomycin, (b) Reacting the product of the step (a) just above with 2,2-dimethoxypropane in the presence of p-toluenesulfonic acid to produce 2″-N-benzyloxycarbonyl-3″-epi-3′,3′a-O-isopropylidene-dihydrostreptomycin, (c) Reacting the product of the step (b) just above with acetic anhydride in the presence of sodium acetate to produce tetra-$N^G$-acetyl-2,5,6,3″,4″,6″-hexa-O-acetyl-2″-N-benzyloxycarbonyl-3″-epi-3,3′a-O-isopropylidene-dihydrostreptomycin, (d) Hydrolyzing the product of the step (c) just above with aqueous acetic acid to produce tetra-$N^G$-acetyl-2,5,6,3″,6″-hexa-O-acetyl-2″-N-benzyloxycarbonyl-3″-epidihydrostreptomycin, (e) Oxidizing the 3′-hydroxymethyl group of the product of the step (d) just above by reacting the latter compound with dimethylsulfoxide in the presence of pyridine, trifluoroacetic acid and dicyclohexylcarbodiimide to produce tetra-$N^G$-acetyl-2,5,6,3",4",6"-hexa-O-acetyl-2"-N-benzyloxycarbonyl-3"-epistreptomycin, (f) Removing all the acetyl groups from the product of the step (e) just above by hydrolysis to produce 2"-N-benzyloxycarbonyl-3"-epistreptomycin, and (g) Subjecting the 2"-N-benzyloxycarbonyl-3"-epistreptomycin to a catalytic hydrogenolysis to remove the 2"-N-benzyloxycarbonyl group therefrom and thus to produce the desired 3"-epistreptomycin.

We have further found it also possible to produce 3"-epidihydrostreptomycin of the formula (I') through a route different from the route of the process according to the first flow diagram, via the 2"-N-benzyloxycarbonyl-dihydrostreptomycin of the formula (2) obtained as an intermediate product. Thus, a further process of producing 3"-epidihydrostreptomycin via the intermediate compound of the formula (2) is briefly shown in the following third flow diagram and is fully illustrated by Example 3 given later. The third flow diagram is shown in brief similarly to the first and second flow diagrams in such way that the intermolecular sites of the compound which just have undergone chemical change or modification at one particular reaction stage are preferentially shown while such sites of the compound which are remaining unchanged at that particular reaction stage are not shown in the third flow diagram.

Third Flow Diagram

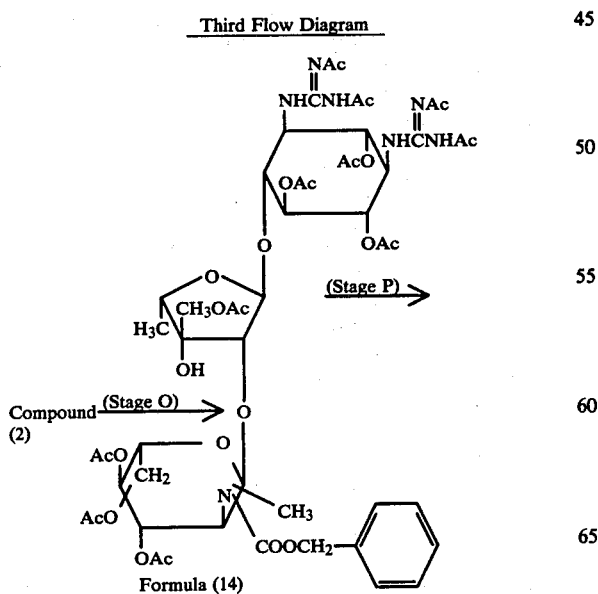

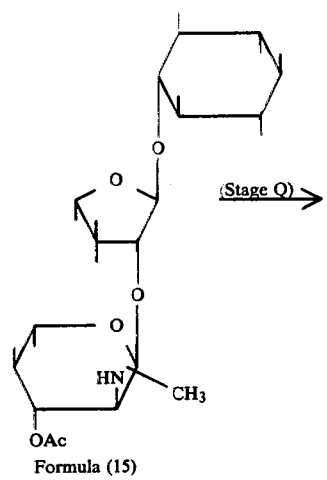

Formula (15)

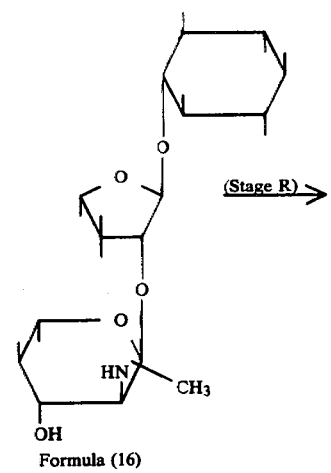

Formula (16)

Formula (17)

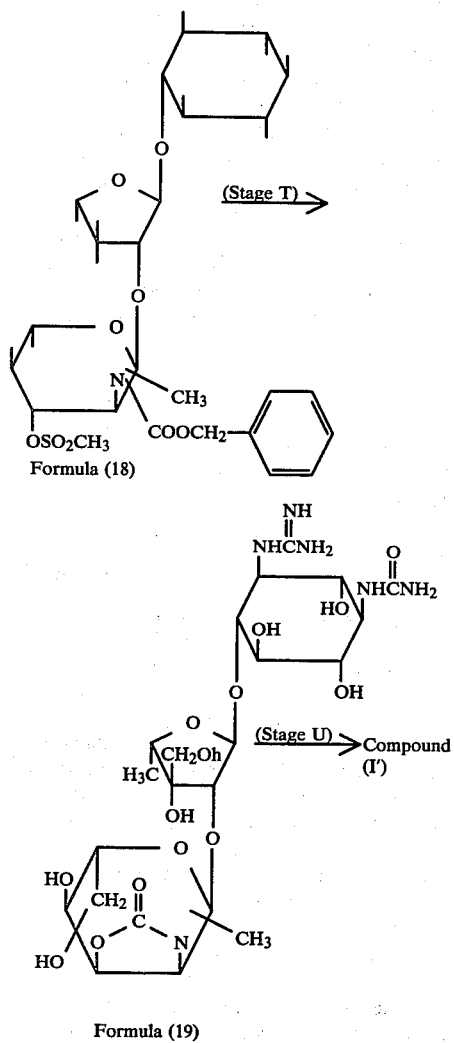

Formula (18)

Formula (19)

In the process according to the third flow diagram as above, Stage O of this process is to effect the protective N,O-acetylation of the 2″-N-benzyloxycarbonyl-dihydrostreptomycin, namely the compound of the formula (2) shown in the first flow diagram and may be conducted in a similar manner to Stage C of the process according to the first flow diagram or to Stage K of the process according to the second flow diagram. In Stage O of this process, therefore, the compound of the formula (2) may preferably be reacted with a 11 molar proportion or more of acetic anhydride in the presence of sodium acetate using an excess of the acetic anhydride as the reaction medium to acetylate all the remaining free hydroxyl groups (seven) (excepting the 3′-hydroxyl group) and all the two guanidyl groups of the compound of the formula (2) and thereby to produce tetra-$N^G$-acetyl-2,5,6,3′a,3″,4″,6″-hepta-O-acetyl-2″-N-benzyloxycarbonyldihydrostreptomycin represented by the formula (14) in the third flow diagram.

Step P of this process is to de-benzyloxycarbonylate the compound of the formula (14) and may be carried out in the same manner as in Stage D of the process according to the first flow diagram. Thus, the compound of the formula (14) may be subjected to a conventional catalytic hydrogenolysis with hydrogen in the presence of a known hydrogenolysis catalyst such as palladium black to remove the 2″-N-benzyloxycarbonyl group from said compound and thereby to produce tetra-$N^G$-acetyl-2,5,6,3′a,3″,4″,6″-hepta-O-acetyl-dihydrostreptomycin briefly represented by the formula (15) in the third flow diagram.

Stage Q of this process is to effect a preferential removal of the 3″-O-acetyl group from the compound of the formula (15) and may be carried out in the same manner as in Stage E of the process according to the first flow diagram. Thus, the compound of the formula (15) is dissolved in a volume of ethanol and the resultant ethanolic solution is allowed to stand at a temperature of 20°–30° C. for 1 day or more, whereby the preferential removal of the 3″-O-acetyl gropu from the 3″-hydroxyl group of the compound (15) takes place through ethanolysis. This fact that the blocking acetyl group can be removed only from the 3″-hydroxyl group of the compound (15) while all the other blocking O-acetyl groups are not cleaved out of the compound (15) is unexpectable and surprising. Through this Stage Q, there is produced tetra-$N^G$-acetyl-2,5,6,3′a,4″,6″-hexa-O-acetyl-dihydrostreptomycin briefly represented by the formula (16) in the third flow diagram.

Stage R of this process is to effect re-introduction of benzyloxycarbonyl group into the 2″-methylamino group of the compound of the formula (16) and may be conducted in the same manner as in Stage F of the process according to the first flow diagram. Thus, the compound of the formula (16) may either be reacted with benzyloxycarbonyl chloride in a mixture of water and acetone under icecooling in the presence of an alkali metal carbonate or may be reacted with benzyloxycarbonyl chloride in chloroform in the presence of sodium hydrogen carbonate. By this Stage R, there is produced tetra-$N^G$-acetyl-2,5,6,3′a,4″-hexa-O-acetyl-2″-N-benzyloxycarbonyl-dihydrostreptomycin briefly represented by the formula (17) in the third flow diagram.

Stage S of this process is to methanesulfonylate the 3″-hydroxyl group of the compound of the formula (17) and may be conducted by reacting the compound (17) with a 1 molar or substantially 1 molar proportion of methanesulfonyl chloride in pyridine at a temperature of −50° C. to +50° C. By this Stage S, there is produced tetra-$N^G$-acetyl-2,5,6,3′a,4″,6″-hexa-O-acetyl-2″-N-benzyloxycarbonyl-3″-O-methylsulfonyl-dihydrostreptomycin briefly represented by the formula (18) in the third flow diagram.

Stage T of the present process is to convert the compound of the formula (18) into a 2″,3″-N,O-carbonylated derivative thereof. For this purpose, the compound of the formula (18) may be dissolved in a volume of 2-methoxy-ethanol and the resultant solution is heated to an elevated temperature of 50° C. to 100° C. in the presence of sodium acetate, or alternatively the compound of the formula (18) may be reacted with sodium methylate in methanol at a temperature of −20° C.~+50° C., preferably at ambient temperature, whereby the 3″-methylsulfonyloxy group is interacted and condensed with the 2″-benzyloxycarbonyl-(methyl)amino group, so that the cyclisation reaction occurs to form the 2″,3″-N,O-carbonyl group (the cyclic 2″,3″-N,O-carbamate group), with concomitantly involving the reaction for removal of all the acetyl groups. In this way, there is produced 2″,3″-N,O-carbonyl-3″-epidihydrostreptomycin of the formula (19) shown in the third flow diagram (see Example 3(f), (g) given later).

Stage U of the present process is to effect the hydrolytic ring-fission of the cyclic cis-2",3"-N,O-carbamate group of the compound of the formula (19). Thus, this Stage U may be accomplished by hydrolyzing the compound of the formula (19) with water in the presence of barium hydroxide in tetrahydrofuran, whereby the 2",3"-N,O-carbonyl group (the cyclic 2",3"-N,O-carbamate group) can be removed by the ring-fission thereof from the compound of the formula (19) and the 3"-hydroxyl group so liberated is remaining inversed in the epi-position, to afford the desired 3"-epidihydrostreptomycin, namely the compound of the formula (I') in the third flow diagram.

According to a fourth embodiment of this invention, therefore, there is provided a process for the production of 3"-epidihydrostreptomycin, which comprises the consecutive steps of:

(a) Reacting tetra-N$^G$-acetyl-2,5,6,3'a, 3",4",6"-hepta-O-acetyl-dihydrostreptomycin of the formula

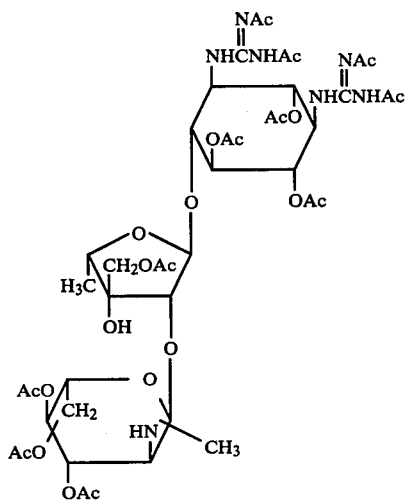

wherein Ac denotes an acetyl group, with ethanol at a temperature of 20°–30° C. to effect preferential removal of the 3"-O-acetyl group from the above-mentioned N,O-acetylated dihydrostreptomycin compound and thereby to produce tetra-N$^G$-acetyl-2,5,6,3'a,4",6"-hexa-O-acetyldihydrostreptomycin, (b) Reacting the product of the step (a) just above with benzyloxycarbonyl chloride to produce tetra-N$^G$-acetyl-2,5,6,3'a,4",6"-hexa-O-acetyl-2"-N-benzyloxycarbonyldihydrostreptomycin, (c) Reacting the product of the step (b) just above with methanesulfonyl chloride in pyridine to produce tetra-N$^G$-acetyl-2,5,6,3'a,4",6"-hexa-O-acetyl-2"-N-benzyloxycarbonyl-3"-O-methylsulfonyl-dihydrostreptomycin, (d) Reacting the product of the step (c) just above either with 2-methoxyethanol at a temperature of 50° C. to 100° C. or with sodium methylate in methanol at a temperature of −20° C.∼50° C., to produce 2",3"-N,O-carbonyl-3"-epi-dihydrostreptomycin, and (e) Hydrolyzing the product of the step (d) just above with water in the presence of barium hydroxide to remove the 2",3"-N,O-carbonyl group therefrom and thus to produce the desired 3"-epidihydrostreptomycin.

As stated hereinbefore, the new compounds of this invention, namely 3"-epistreptomycin and 3"-epidihydrostreptomycin are of a low toxicity. The new compounds of this invention are each effective in therapeutic treatment of bacterial infections when administered intramuscularly in a dosage of from about 100 mg to about 1000 mg per day in divided dosages three or four times a day. Generally, the new compounds of this invention may be administered orally, intraperitoneally, intravenously or intramuscularly using any pharmaceutical form known in the art for such administration and in a similar manner to streptomycin and dihydrostreptomycin. Examples of pharmaceutical forms for oral administration are powders, capsules, tablets, syrup and the like. The new compounds of this invention may also be formulated into an aqueous injectable solution.

According to a fifth embodiment of this invention, therefore, there is provided an antibacterial composition comprising an antibacterially effective amount of 3"-epistreptomycin or 3"-epidihydrostreptomycin as the active ingredient, in combination with a pharmaceutically acceptable carrier for the active ingredient.

This invention is now illustrated with reference to the following Examples which show the production of the new compounds of this invention.

EXAMPLE 1

Synthesis of 3"-epidihydrostreptomycin (a) Production of 2"-N-benzyloxycarbonyl-dihydrostreptomycin sulfate (stage A)

Dihydrostreptomycin 3/2 sulfate (73 g) was dissolved in a mixture of 1 l. of water and 1 l. of acetone, and 16 g of sodium carbonate was dissolved in the resulting solution of dihydrostreptomycin, which was then cooled to 0° C. Benzyloxycarbonyl chloride (30 ml) was admixed with the cooled solution under stirring, and the admixture obtained was kept at 0° C. for 4 hours and then at ambient temperature for 15 hours to effect the reaction for the introduction of benzyloxycarbonyl group into the 2"-methylamino group of dihydrostreptomycin.

The reaction solution was neutralized by addition of 2M aqueous sulfuric acid and then concentrated to a volume of 70 ml under reduced pressure. The concentrated solution was extracted with ethyl acetate and the remaining aqueous phase of said solution was separated and concentrated under reduced pressure to give a solid. This solid was taken up into methanol and the resultant methanolic solution was filtered to remove the insoluble matter therefrom. The methanolic solution (the filtrate) was then concentrated under reduced pressure to afford the above titled compound (corresponding to the formula (2) shown in the first flow diagram). Yield 80 g. (98%).

(b) Production of 2"-N-benzyloxycarbonyl-3',3'a;4",6"-di-O-isopropylidene-dihydrostreptomycin carbonate (stage B)

The substance (4.98 g) obtained in the above stage A of this Example was dissolved in 100 ml of dry dimethylformamide, into which was then dissolved 330 mg of p-toluenesulfonic acid. The resultant solution was admixed with 4.5 ml of 2,2-dimethoxy-propane, followed by heating at 40° C. for 18 hours to effect the reaction for introduction of the 3',3'a; 4",6"-di-O-isopropylidene groups. During this reaction, 220 mg portions of p-toluenesulfonic acid were added to the reaction solution at three times of 5 hours, 8 hours and 15 hours after the beginning of the reaction to adjust the reaction solution at pH 4. After completion of the reaction, the reaction solution was admixed with 0.4 ml of triethylamine and then concentrated to a small volume. A volume of ethyl ether was added to the concentrated solution to deposit a precipitate. This precipitate was removed by filtration, well washed with ethyl ether and then taken up into water. The aqueous solution obtained was passed through a column of an ion-exchange resin, Dowex 1×2 (Cl⁻ form) and the effluent from the resin column was concentrated to dryness. The resultant solid residue comprising a mixture of different isopropylidenation products was subjected to column chromatography on silica gel developed with benzene-pyridine-ehtanol-water-acetic acid (12:6:6:2:1 by volume) for isolation and purification of the products, to afford the above titled compound (represented by the formula (3) in the first flow diagram). Yield 2.08 g (39%).

The titled compound (carbonate) showed a specific optical rotation $[\alpha]_D^{23} - 67°$ (c 1, water).

Elemental analysis: Found: C 50.21, H 6.74, N 11.71%; Calcd. for $C_{35}H_{55}N_7O_{14}.H_2CO_3$: C 50.28, H 6.68, N 11.40%.

(c) Production of tetra-$N^G$-acetyl-2,5,6,3″-tetra-O-acetyl-2″-N-benzyloxycarbonyl-3′,3′a;4″,6″-di-O-isopropylidene-dihydrostreptomycin (stage C)

The substance (3.75 g) obtained in the above stage C of this Example was suspended in 38 ml of acetic anhydride, to which was then added 3.54 g of anhydrous sodium acetate. The suspension obtained was stirred vigorously at 75° C. for 18 hours to effect the reaction for introduction of acetyl groups.

After cooling to ambient temperature, the reaction solution was concentrated to a small volume and cyclohexane was added to the concentrated solution to deposit a precipitate. The precipitate was removed by filtration, well washed with cyclohexane and taken up into chloroform. The solution so obtained was washed with aqueous saturated sodium hydrogen carbonate and then with water, dried over anhydrous sodium sulfate and concentrated to dryness under reduced pressure. The solid residue obtained was purified by a column chromatography on silica gel developed with toluene-acetate (4:1) to afford the above titled compound (represented by the formula (4) in the first flow diagram). Yield 2.4 g (49%). $[\alpha]_D^{23} - 39°$ (c 1, chloroform).

Elemental analysis: Found: C 53.15, H 6.21, N 8.40%; Calcd. for $C_{51}H_{71}N_7O_{22}.H_2O$: C 53.16, H 6.39, N 8.51%.

(d) Production of tetra-$N^G$-acetyl-2,5,6,3″-tetra-O-acetyl-3′,3′a;4″,6″-di-O-isopropylidene-dihydrostreptomycin (stage D)

The substance (22.1 mg) obtained in the above stage C of this Example was taken up into 0.4 ml of ethanol and subjected to hydrogenolysis with gaseous hydrogen at 1 atm. at ambient temperature for 2 hours in the presence of palladium black as added to the ethanolic solution (to effect the reaction for removal of the 2″-N-benzyloxycarbonyl group). The reaction solution was filtered to remove the catalyst, and the filtrate was concentrated to dryness. The solid residue obtained was purified by column chromatography on silica gel developed with chloroform-ethanol (18:1) to afford the above titled compound (represented by the formula (5) in the first flow diagram). Yield 16.8 mg (86%) $[\alpha]_D^{23} - 48°$ (c 1, chloroform).

Elemental analysis: Found: C 50.35, H 6.31, N 9.38%; Calcd. for $C_{43}H_{65}N_7C_{20}.1/2H_2CO_3.1/2H_2O$: C 50.23, H 6.49, N 9.43%.

(e) Production of tetra-$N^G$-acetyl-2,5,6-tri-O-acetyl-3′,3′a;4″,6″-O-isopropylidene-dihydrostreptomycin (stage E)

The substance (299 mg) obtained in the above stage D of this Example was dissolved in 6 ml of ethanol, and the ethanolic solution was allowed to stand at 27° C. for 3 days to effect the reaction for preferential cleavage of the 3″-O-acetyl group. The reaction solution was concentrated to dryness under reduced pressure, and the solid residue obtained was subjected to column chromatography on silica gel developed with chloroform-ethanol (15:1) for isolation and purification of the desired reaction product to afford the above titled compound (represented by the formula (6) in the first flow diagram). Yield 100 mg (35%).

$[\alpha]_D^{23} - 48°$ (c 1, chloroform).

Elemental analysis: Found: C 49.95, H 6.13, N 10.17%; Calcd. for $C_{41}H_{63}N_7O_9.1/2H_2CO_3$: C 50.40, H 6.52, N 9.91%.

(f) Production of tetra-$N^G$-acetyl-2,5,6-tri-O-acetyl-2″-N-benzyloxycarbonyl-3′,3′a;4″,6″-di-O-isopropylidene-dihydrostreptomycin (stage F)

The substance (23.2 mg) obtained in the above stage E of this Example was dissolved in 4.2 ml of chloroform, to which was then added 2.8 ml of an aqueous solution of 0.7% sodium hydrogen carbonate. The suspension so obtained was cooled to 0° C. and admixed with 0.013 ml of benzyloxycarbonyl chloride under stirring. The resulting admixture was kept at 0° C. for 30 minutes and then at ambient temperature for 1 hour under stirring to effect the reaction for re-introduction of the 2″-N-benzyloxycarbonyl group. The reaction solution was allowed to be separated into the aqueous layer and the chloroform layer, and the latter chloroform layer was removed, washed with water, dried over anhydrous sodium sulfate and concentrated under reduced pressure. The oily product so obtained was admixed with hexane to deposit a precipitate. This precipitate was removed by filtration, well washed with hexane and then purified by column chromatography on silica gel developed with benzene-acetone (7:3) to afford the above titled compound. Yield 25.8 mg (98%).

$[\alpha]_D^{23} - 52°$ (c 1, chloroform).

Elemental analysis: Found: C 53.47, H 6.41, N 9.30%; Calcd. for $C_{49}H_{69}N_7O_{21}$: C 53.89, H 6.37, N 8.98%.

(g) Production of tetra-$N^G$-acetyl-2,5,6-tri-O-acetyl-2″,3″-N,O-carbonyl-3″-epi-3′,3′a;4″,6″-di-O-isopropylidene-dihydrostreptomycin of the following formula (stage G)

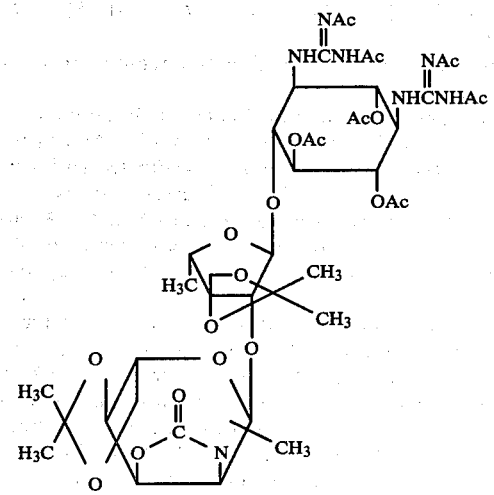

wherein Ac denotes an acetyl group.

The substance (529 mg) obtained in the above stage F of this Example was dissolved in 12 ml of anhydrous dichloromethane, to which was then added 1.3 ml of dry pyridine. The solution obtained was cooled to a temperature of −50° C. and then admixed with 0.182 ml of trifluoromethanesulfonic acid anhydride, followed by reaction at 5° C. for 3.5 hours. The reaction solution was again cooled to a temperature of −50° C. and then admixed with 0.3 ml of dry pyridine and 0.05 ml of trifluoromethanesulfonic acid anhydride, followed by reaction at 5° C. for further 2 hours, whereby there was produced tetra-$N^G$-acetyl-2,5,6-tri-O-acetyl-2''-N-benzyloxycarbonyl-3''-O-trifluoromethylsulfonyl-3',3'a;-4'',6''-di-O-isopropylidene-dihydrostreptomycin. Several drops of water were added to the reaction solution containing the above-mentioned 3''-O-trifluoromethylsulfonylated product, and this solution was allowed to stand at ambient temperature for 30 minutes. Thereafter, the reaction solution was diluted with chloroform and washed with 10% aqueous potassium hydrogen sulfate, with aqueous saturated sodium hydrogen carbonate and then with water. The solution washed was dried over anhydrous sodium sulfate and concentrated to dryness under reduced pressure to afford the 3''-O-trifluoromethylsulfonylated product as a glassy material. This material was dissolved in 12 ml of pyridine and the solution in pyridine was heated at 65° C. for 1 hour to effect the reaction for condensation of the 3''-trifluoromethylsulfonyloxy group with the 2''-benzyloxycarbonyl (methyl)amino group and thereby to form the cyclic 2'',3''-N,O-carbamate group in the N,O-protected dihydrostreptomycin compound, with concomitant inversion of the configuration at C-3''. The reaction solution containing the above titled compound as formed was concentrated under reduced pressure and the solid residue obtained was taken up into chloroform. The resultant solution in chloroform was washed with 10% aqueous potassium hydrogen sulfate, with aqueous saturated sodium hydrogen carbonate and then with water, dried and concentrated to dryness under reduced pressure. The solid residue obtained was purified by column chromatography on silica gel developed with benzene-acetone (9:5) to give the above titled compound (represented by the formula (8) in the first flow diagram). Yield 244 mg (46%).

$[\alpha]_D^{23}$ −60° (c 1, chloroform).

Elemental analysis: Found: C 50.38, H 5.86, N 9.53%; Calcd. for $C_{42}H_{61}N_7O_{20}\cdot H_2O$: C 50.34, H 6.34, N 9.79%.

(h) Production of 3''-epidihydrostreptomycin carbonate (stage H)

The substance (193 mg) obtained in the above stage G of this Example was dissolved in 6 ml of tetrahydrofuran, and the resultant solution was admixed with 4 ml of an aqueous solution of 5.5% of barium hydroxide. The admixture obtained was agitated at 40° C. for 40 hours to effect the reaction for hydrolytic removal of the acetyl groups and 2'',3''-N,O-carbonyl group by hydrolysis.

Gaseous carbon dioxide was passed into the reaction solution, which was then filtered to remove out the precipitate. The filtrate was concentrated to dryness under reduced pressure and the solid residue was taken up into 75% aqueous acetic acid. The solution obtained was heated at 55° C. for 71 hours to effect the reaction for removal of the isopropylidene groups. The reaction solution was concentrated under reduced pressure, and the glassy solid so obtained was dissolved in water. The aqueous solution was placed in a column of 10 ml of an ion-exchange resin, Amberlite CG-50 $NH_4$ form), and this column was developed with aqueous ammonium carbonate according to a gradient elution technique. The eluate from the Amberlite column was collected in 1 ml-fractions, and the active fractions Nos. 10 to 15 containing the aimed product were combined together and concentrated under reduced pressure. The concentrated solution was diluted with water and then again concentrated under reduced pressure, and this dilution with water and the concentration of the diluted solution were repeated several times until ammonium carbonate could not be detected in a last concentrated solution. In this way, the above titled compound (represented by the formula (I') in the first flow diagram) was obtained as a colorless solid having no definite melting point. Yield 22 mg (17%).

$[\alpha]_D^{23}$ −79° (c 0.9, water).

Elemental analysis: Found: C 39.63, H 6.47, N 14.33; Calcd. for $C_{21}H_{41}N_7O_{12}\cdot 3/2H_2CO_3$: C 39.94, H 6.55, N 14.49.

Proton nuclear magnetic resonance spectrum (in $D_2O$): $\delta 1.24$ (doublet, 3H, $J_{4',5'}$ 6.5 Hz, c $CH_3$), $\delta 2.39$ (singlet, 3H, $NCH_3$), $\delta 2.81$ (triplet, 1H, $J_{1'',2''}$ 4 Hz, $J_{2'',3''}$ ∼3.5 Hz, H-2''), $\delta 4.25$ (triplet, 1H, $J_{3'',4''}$ ∼3 Hz, H-3'').

EXAMPLE 2

Synthesis of 3''-epistreptomycin (a) Production of 2''-N-benzyloxycarbonyl-3''-epidihydrostreptomycin dihydrochloride (stage I)

3''-Epidihydrostreptomycin carbonate (124 mg) was dissolved in a mixture of 2.1 ml of water and 1.1 ml of acetone, into which was further dissolved 23 mg of anhydrous sodium carbonate. The solution so obtained was cooled to 0° C. and admixed with 0.033 ml of benzyloxycarbonyl chloride under stirring. The resultant admixture was kept at 0° C. for 1 hour and then at ambient temperature for 4 hours to effect the reaction for introduction of the 2''-N-benzyloxycarbonyl group. The reaction solution was then concentrated to dryness under reduced pressure while adjusting the solution to about pH 7 by addition of 1M aqueous hydrochloric acid. The solid residue obtained was dissolved in hot ethanol and the ethanolic solution was filtered to remove out the insoluble matter. The ethanolic solution as filtered was concentrated to dryness undre reduced pressure and the solid residue was taken up into a small volume of water, followed by passing the resultant aqueous solution through a column of an ion-exchange resin, Dowex 1×2 (Cl⁻ form). The effluent from the resin column was concentrated to dryness under reduced pressure to give the above titled compound (represented by the formula (9) in the second flow diagram) in the form of its dihydrochloride. Yield 87 mg (60%).

$[\alpha]_D^{23}$ −66° (c 1, water).

(b) Production of 2''-N-benzyloxycarbonyl-3''-epi-3',3'a-O-isopropylidene-dihydrostreptomycin dihydrochloride (stage J)

The substance (98 mg) obtained in the above stage I of this Example was dissolved in 1.3 ml of anhydrous dimethylformamide, into which was then dissolved 3.3 mg of p-toluenesulfonic acid. The solution so obtained was admixed with 0.1 ml of 2,2-dimethoxypropane and the resultant admixture was kept at 40° C. for 8 hours to effect the reaction for introduction of the 3',3'a-O-isopropylidene group. Triethylamine (0.04 ml) was added to the reaction solution, which was then concentrated to a small volume under reduced pressure. The concentrated solution was admixed with ethyl ether to deposit a precipitate. This precipitate was removed by filtration and well washed with ethyl and then the solid was dissolved in 1.6 ml of a mixture of acetic acid-methanol (1:4). The resultant solution was kept at 50° C. for 4 hours to effect the reaction for removal of such isopropylidene groups which occasionally had been undesirably introduced into the hydroxyl groups other than the 3'- and 3'a-positions of the dihydrostreptomycin compound. The reaction solution so formed was concentrated to a small volume under reduced pressure and then admixed with acetone to deposit a precipitate. This solid (the precipitate) was purified by column chromatography on cellulose developed with pyridine-ethyl acetate-10% aqueous acetic acid (2:2:1), and such fractions of the eluate containing the desired product were combined together and concentrated to dryness under reduced pressure. The solid residue obtained was dissolved in water and the resultant aqueous solution was passed through a column of an ion-exchange resin, Dowex 1×2 (Cl$^-$ form). The effluent from this resin column was concentrated to dryness under reduced pressure to give the above titled compound (represented by the formula (10) in the second flow diagram) in the form of its dihydrochloride.

Yield 36 mg (35%). $[\alpha]_D^{23} -65°$ (c 1, water).

Elemental analysis: Found: C 46.02, H 6.81, N 11.55, Cl 8.97% Calcd. for $C_{32}H_{51}N_7O_{14}.2HCl$: C 46.27, H 6.43, N 11.80, Cl 8.54%.

(c) Production of tetra-$N^G$-acetyl-2,5,6,3'',4'',6''-hexa-O-acetyl-2''-N-benzyloxycarbonyl-3''-epi-3',3'a-O-isopropylidene-dihydrostreptomycin (stage K)

The substance (78 mg) obtained in the above stage J of this Example was suspended in 1.65 ml of acetic anhydride, to which was then added 88 mg of anhydrous sodium acetate. The admixture obtained was vigorously agitated at 75° C. for 18 hours to effect the reaction for introduction of acetyl groups. The reaction solution was cooled to ambient temperature and concentrated to a small volume under reduced pressure, followed by admixing the concentrated solution with cyclohexane to deposit a precipitate. This precipitate was removed by filtration, well washed with cyclohexane and then dissolved in chloroform. The resultant solution in chloroform was washed with aqueous saturated sodium hydrogen carbonate and then with water, dried over anhydrous sodium sulfate and concentrated to dryness under reduced pressure. The solid residue obtained was purified by column chromatography on silica gel developed with chloroform-ethanol (30:1) to afford the title compound (represented by the formula (11) in the second flow diagram). Yield 76.3 mg (69%). $[\alpha]_D^{23} -41°$ (c 1, chloroform).

(d) Production of tetra-$N^G$-acetyl-2,5,6,3'',4'',6''-hexa-O-acetyl-2''-N-benzyloxycarbonyl-3''-epidihydrostreptomycin (stage L)

The substance (83 mg) obtained in the above stage K of this Example was dissolved in 3.4 ml of a mixture of dioxane-water-acetic acid (1:1:6), and the resultant solution was kept at 55° C. for 50 hours to effect the reaction for removal of the 3',3'a-O-isopropylidene group by hydrolysis. The reaction solution was admixed with toluene and then concentrated, and further admixing of the concentrated solution with a fresh volume of toluene and concentrating of the admixture were repeated several times. A final concentrated solution of a small volume was admixed with cyclohexane to deposit a precipitate. This precipitate was removed by filtration and well washed with cyclohexane and then the solid was purified by column chromatography on silica gel developed with chloroform-ethanol (25:1) to give the above titled compound (represented by the formula (12) in the second flow diagram). Yield 46.5 mg (58%). $[\alpha]_D^{23} -42°$ (c 1, chloroform).

(e) Production of 2''-N-benzyloxycarbonyl-3''-epistreptomycin dihydrochloride (stage M)

The substance (63 mg) obtained in the above stage L of this Example was dissolved in 0.35 ml of anhydrous dimethylsulfoxide, to which were then added 0.035 ml of pyridine and 0.018 ml of trifluoroacetic acid as well as a solution of 82 mg of dicyclohexylcarbodiimide in 0.4 ml of anhydrous dimethylsulfoxide. The admixture obtained was kept at ambient temperature for 90 minutes under stirring to effect the reaction of oxidizing the 3'-hydroxymethyl group into the aldehyde group, so that tetra-$N^G$-acetyl-2,5,6,3'',4'',6''-O-hexa-O-acetyl-2''-N-benzyloxycarbonyl-3''-epistreptomycin was produced. The reaction solution was filtered to remove the insoluble matter (comprising N,N-di-cyclohexyl urea), and the filtrate was well washed with cyclohexane, diluted with chloroform, washed with aqueous saturated sodium chloride and dried. The dried solution was concentrated to dryness under reduced pressure. The solid obtained was dissolved in 2.8 ml of a mixture of concentrated aqueous ammonia-methanol (1:14), and the resultant solution was kept at ambient temperature for 3 hours to effect the reaction for removal of the acetyl groups. The reaction solution containing 2''-N-Benzyloxycarbonyl-3''-epistreptomycin as formed was concentrated under reduced pressure and the solid obtained was dissolved in water, followed by filtering the aqueous solution to remove the insoluble matter. The filtrate was purified by column chromatography on Dowex 1×2 resin (Cl$^-$ form, 3 ml) developed with water. The eluate from the resin column was collected in 0.5 ml-fractions and the fractions Nos. 5 to 8 containing the desired compound were combined together. The combined solution was neutralized by addition of 0.1M aqueous hydrochloric acid, concentrated to a small volume and then adjusted to a pH of about 4 by addition of 0.1M aqueous hydrochloric acid, further followed by admixing the solution with acetone to deposit a precipitate. This precipitate was removed by filtration and well washed with acetone to give the titled compound (represented by the formula (13) in the second flow diagram) in the form of its dihydrochloride. Yield 4.8 mg (11%).

$[\alpha]_D^{23} -66°$ (c 1, water).

Proton nuclear magnetic resonance spectrum (in $D_2O$): δ3.05 (singlet, 3H, NCH$_3$).

(f) Production of 3''-epistreotomycin trihydrochloride (stage N)

The substance (26 mg) obtained in the above stage M of this Example was dissolved in 0.9 ml of water, to which was then added about 0.05 ml of Raney nickel under well stirring. The admixture so obtained was filtered, and the filtrate was adjusted to pH 4 by addition of acetic acid, admixed with about 0.15 ml of palladium black as the hydrogenolysis catalyst and then subjected to hydrogenolysis with hydrogen gas at a hydrogen pressure of 3 kg/cm$^2$ for 1 hour at ambient temperature. The reaction mixture was filtered to remove the catalyst, and the filtrate was concentrated to dryness under reduced pressure. The solid residue obtained was purified by column chromatography on Dowex 1×2 resin (Cl⁻ form) developed with water to afford the above titled compound (represented by the formula (I″) in the second flow diagram) in the form of its trihydrochloride monohydrate as a colorless solid having no definite melting point. Yield 13.2 mg (56%).

$[\alpha]_D^{23}$ −80° (c 1, water).

Elemental analysis: Found: C 35.22, H 6.51, N 13.58%; Calcd. for $C_{21}H_{39}N_7O_{12} \cdot 3HCl \cdot H_2O$: C 35.58, H 6.26, N 13.83%.

EXAMPLE 3

Synthesis of 3″-epidihydrostreptomycin (a) Production of tetra-$N^G$-acetyl-2,5,6,3′a,3″,4″,6″-hepta-O-acetyl-2″-N-benzyloxycarbonyl-dihydrostreptomycin (stage O)

2″-N-Benzyloxycarbonyl-dihydrostreptomycin (18.0 g) obtained in the stage A of Example 1 was suspended in 180 ml of acetic anhydride, to which was then added 18 g of anhydrous sodium acetate. The admixture obtained was vigorously stirred at 75° C. for 18 hours to effect the reaction for introduction of the acetyl groups. The reaction solution was cooled to ambient temperature and then concentrated to dryness under reduced pressure. The residue obtained was extracted with 1.2 l. of chloroform and the resultant extract in chloroform was washed three times with 50 ml portions of aqueous saturated sodium hydrogen carbonate and three times with 50 ml portions of water. The organic phase (the solution in chloroform) so washed was then dried over anhydrous sodium sulfate and concentrated under reduced pressure. The residue obtained was dissolved in chloroform and then precipitated from the solution by addition of hexane, and the solid obtained was washed with hexane and dried to afford the above titled compound (represented by the formula (14) in the third flow diagram). Yield 25.5 g (98%).

$[\alpha]_D^{23}$ −72° (c 1, chloroform).

Elemental analysis: Found: C 52.01, H 5.92, N 8.35%; Calcd. for $C_{51}H_{69}N_7O_{25}$: C 51.90, H 5.89, N 8.31%.

(b) Production of tetra-$N^G$-acetyl-2,5,6,3′a,3″,4″,6″-hepta-O-acetyl-dihydrostreptomycin (stage P)

The substance (1.896 g) obtained in the above stage O of this Example was dissolved in 20 ml of ethanol, to which was then added a quantity of palladium black as the hydrogenolysis catalyst. The resultant admixture was reacted with hydrogen at atmospheric pressure and at ambient temperature for 1 hour to effect the reaction for removal of the 2″-N-benzyloxycarbonyl group by hydrogenolysis. The reaction mixture was filtered to remove the catalyst, and the filtrate was concentrated. As the hydrogenolysis proceeded substantially quantitatively, the above titled compound (represented by the formula (15) in the third flow diagram) was afforded in a yield of 1.562 g (93%). $[\alpha]_D^{23}$ −82° (c 1, chloroform).

Elemental analysis: Found: C 49.17, H 6.09, N 9.12%; Calcd. for $C_{43}H_{63}N_7O_{23}$: C 49.38, H 6.07, N 9.37%.

(c) Production of tetra-$N^G$-acetyl-2,5,6,3′a,4″,6″-hexa-O-acetyl-dihydrostreptomycin (stage Q)

The substance (513 mg) obtained in the stage P of this Example was dissolved in 10 ml of ethanol and the ethanolic solution was kept at 25° C. for 35 hours to effect the reaction for preferential removal of the 3″-O-acetyl group. During the reaction time, a stream of gaseous carbon dioxide was slowly passed into the reaction solution to adjust the pH of the reaction solution to pH 7. The reaction solution was concentrated under reduced pressure and the solid obtained was subjected to column chromatography on silica gel developed with chloroform-ethanol (10:1) for isolation and purification of the aimed product, whereby the above titled compound (represented by the formula (16) in the third flow diagram) was afforded in a yield of 222 mg (43%). $[\alpha]_D^{25}$ −71° (c 1, chloroform). The starting substance which remained unreacted was recovered in a yield of 194 mg.

Elemental analysis: Found: C 48.86, H 6.07; N 9.54%; Calcd. for $C_{41}H_{61}N_7O_{22}$: C 49.05, H 6.12, N 9.77%.

(d) Production of tetra-$N^G$-acetyl-2,5,6,3′a,4″,6″-hexa-O-acetyl-2″-N-benzyloxycarbonyl-dihydrostreptomycin (stage R)

The substance (979 mg) contained in the stage Q of this Example was dissolved in 180 ml of chloroform, to which was then added 120 ml of 0.7% aqueous sodium hydrogen carbonate. The suspension so obtained was cooled to 0° C. and admixed with 0.55 ml of benzyloxycarbonyl chloride under stirring. The mixture obtained was kept at 0° C. for 30 minutes and then at ambient temperature for 30 minutes under stirring to effect the reaction for re-introduction of the 2″-N-benzyloxycarbonyl group. The reaction solution was allowed to stand and was thus separated into the aqueous phase and the chloroform phase. The chloroform phase was removed by decantation, washed with water, dried and concentrated under reduced pressure. The oily product so obtained was admixed with cyclohexane to deposit a precipitate. This precipitate was removed by filtration and well washed with cyclohexane, and this solid was then purified by column chromatography on silica gel developed with chloroform-ethanol (20:1) to give the above titled compound (represented by the formula (17) in the third flow diagram). Yield 817 mg (74%).

$[\alpha]_D^{20}$ −71° (c 1, chloroform).

(e) Production of tetra-$N^G$-acetyl-2,5,6,3′a,4″,6″-hexa-O-acetyl-2″-N-benzyloxycarbonyl-3″-O-methylsulfonyldihydrostreptomycin (stage S)

The substance (975 mg) obtained in the stage R of this Example was dissolved in 34 ml of pyridine, to which was then added 0.5 ml of methanesulfonyl chloride at 0° C. The resultant mixture was kept at 0° C. for 1 hour and then at ambient temperature for 1 hour to effect the reaction for introduction of the 3″-O-methylsulfonyl group. The reaction solution was cooled to 0° C., admixed with a small volume of water and allowed to stand for several minutes and then poured into 60 ml of water. The admixture obtained was extracted with 100 ml of chloroform. The organic layer (the resultant extract in chloroform) was washed with aqueous saturated sodium hydrogen carbonate and then with aqueous saturated sodium chloride, dried over anhydrous sodium sulfate and concentrated to dryness under reduced pressure. The solid residue obtained was purified by column chromatography on silica gel using chloroformethanol (25:1) as the development solvent to afford the above titled compound (represented by the formula (18) in the third flow diagram). Yield 944 mg (91%).

$[\alpha]_D^{25}$ −72° (c 1, chloroform).

Elemental analysis: Found: C 49.09, H 5.64, N 7.76, S 2.73%; Calcd. for $C_{50}H_{69}N_7O_{26}S$: C 49.38, H 5.72, N 8.06, S 2.64%.

(f) Production of 2″,3″-N,O-carbonyl-3″-epidihydrostreptomycin carbonate (stage T)

The substance (359 mg) obtained in the above stage S of this Example was dissolved in 7 ml of 2-methoxyethanol, into which was then dissolved 358 mg of sodium acetate trihydrate. The solution obtained was kept at 95° C. for 73 hours to effect the reaction for condensation of the 3"-methylsulfonyloxy group with the 2"-benzyloxycarbonyl-methylamino group (for formation of the 2",3"-N,O-carbonyl group), with concomitant reaction for the removal of the acetyl groups. The reaction solution containing the 2",3"-N,O-carbonyl-3"-epidihydrostreptomycin as formed was concentrated under reduced pressure, and the solid residue was dissolved in water. The resultant aqueous solution was passed through a column of an ion-exchange resin, Dowex 1×2 (OH−form, 20 ml) for effecting an ion-exchange column chromatography, using water as the development solvent. The eluate from the resin column was collected in 2 ml-fractions, and the fractions Nos. 9-13 of the eluate containing the desired product were combined together, neutralized by addition of 0.5 M hydrochloric acid and then concentrated under reduced pressure. The solid residue obtained was taken up into water and the aqueous solution was subjected to an ion-exchange column chromatography on an ion-exchange resin, Amberlite CG 50 (NH$_4$+form, 20 ml) using aqueous ammonium carbonate as the eluent according to a gradient elution technique. The eluate was collected in 2 ml-fractions, and the fractions Nos. 15-20 containing the desired product were combined together and concentrated under reduced pressure. The concentrated solution so obtained was diluted with water and then again concentrated under reduced pressure, and dilution of the concentrated solution with water and re-concentration of the diluted solution were repeated several times until the ammonium carbonate could not be detected in a final concentrated solution. In this way, there was obtained as a solid a mixture containing the above titled compound (represented by the formula (19) in the third flow diagram) in a yield of 153 mg (76%).

(g) Production of 2",3"-N,O-carbonyl-3"-epidihydrostreptomycin carbonate (a modification of the aforesaid stage T)

The tetra-N$^G$-acetyl-2,5,6,3'a,4",6"-hexa-O-acetyl-2"-N-benzyloxycarbonyl-3"-O-methylsulfonyl-dihydrostreptomycin, namely the substance (451 mg) obtained as the solid in the stage S of this Example was dissolved in 9 ml of a solution of 0.2 M sodium methylate in methanol, and the resultant solution was kept at ambient temperature for 2 hour to effect the reaction for the formation of the cyclic 2",3"-N,O-carbamate group with concomittant removal of the acetyl groups.

The reaction mixture was neutralized by addition of 1M aqueous hydrochloric acid and concentrated to dryness under reduced pressure, and the solid residue was dissolved in water, and the aqueous solution was placed into a column of an ion-exchange resin, Amberlite CG-50 (NH$_4$+form, 30 ml), which was then eluted with aqueous ammonium carbonate according to a gradient elution method. The eluate from the resin column was collected in 3 ml-fractions, and the fractions Nos. 20 to 40 containing the desired product were combined together and concentrated under reduced pressure. The concentrated solution obtained wsa diluted with water and again concentrated under reduced pressure, and dilution of the concentrated solution with water and re-concentration of the diluted solution were repeated several times until the ammonium carbonate could not be detected in a final concentrated solution. There was thus obtained the above titled compound (represented by the formula (19) in the third flow diagram) in the form of its carbonate. Yield 157 mg (63%). $[\alpha]_D^{25} -90°$ (c 1, water).

Elemental analysis: Found: C 38.08, H 6.24, N 12.97%; Calcd. for $C_{22}H_{39}N_7O_{13}\cdot2H_2CO_3\cdot H_2O$:

C 38.34, H 6.03, N 13.05%.

(h) Production of 3"-epidihydrostreptomycin (3/2 carbonate) (stage U)

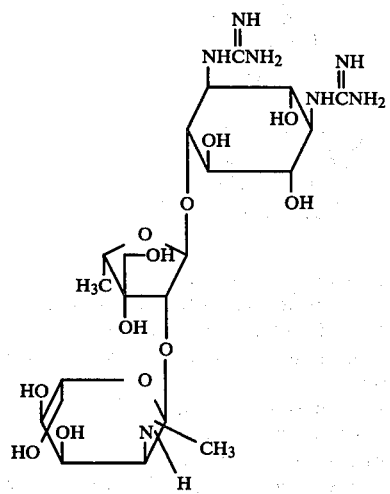

The substance (128 mg) obtained in the stage T of this Example 3(f) was admixed with 3.9 ml of an aqueous solution of 5.5% of barium hydroxide, followed by agitating at 40° C. for 20 hours to effect the reaction for removal of the 2",3"-N,O-carbonyl group (that is, the hydrolytic ring-fission of the cyclic 2",3"-N,O-carbamate group). Gaseous carbon dioxide was passed into the reaction solution to deposit a precipitate comprising barium carbonate, followed by filtering the reaction solution to remove the precipitate as formed. The filtrate was placed in a column of an ion-exchange resin, Amberlite CG-50 (NH$_4$+ form, 10 ml), which was then developed gradiently with aqueous ammonium carbonate as the eluent. The eluate from the resin column was collected in 1 ml-fractions, and the fractions Nos. 15 to 20 containing the aimed product were combined together and concentrated under reduced pressure. The concentrated solution was diluted with water and again concentrated, and dilution of a concentrated solution with water and re-concentration of the diluted solution were repeated several times until the ammonium carbonate could not be detected in a final concentrated solution. There was thus obtained the above titled compound (represented by the formula (I') in the third flow diagram and also shown just above) in the form of its 3/2 carbonate as a colorless solid. Yield 42 mg (36%).

What we claim is:

1. 3"-Epistreptomycin or 3"-epidihydrostreptomycin of the general formula

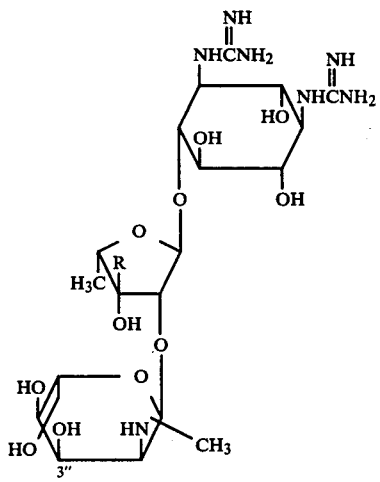

wherein R denotes an aldehyde group—CHO or a hydroxymethyl group—CH₂OH, and a pharmaceutically acceptable acid-addition salt thereof.

2. A compound as claimed in claim 1, which is 3''-epistreptomycin.

3. A compound as claimed in claim 1, which is 3''-epidihydrostreptomycin.

4. A process for the production of 3''-epidihydrostreptomycin, which comprises the consecutive steps of:

(a) reacting tetra-$N^G$-acetyl-2,5,6,3''-tetra-O-acetyl-3',3'a;4'',6''-di-O-isopropylidene-dihydrostreptomycin of the formula

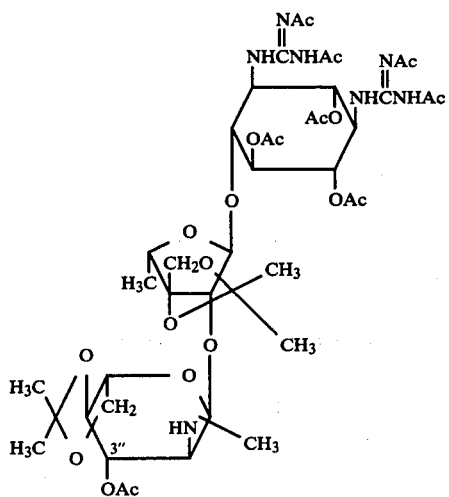

wherein Ac denotes an acetyl group, with ethanol at a temperature of 20–30° C. to effect removal of the 3''-O-acetyl group from the above-mentioned N,O-protected dihydrostreptomycin compound and thereby to produce tetra-$N^G$-acetyl-2,5,6-tri-O-acetyl-3',3'a;4'',6''-O-isopropylidene-dihydrostreptomycin, (b) reacting the product of the step (a) with benzyloxycarbonyl chloride to produce tetra-$N^G$-acetyl-2,5,6-tri-O-acetyl-2''-N-benzyloxycarbonyl-3',3'a;-4'',6''-di-O- isopropylidene-dihydrostreptomycin, (c) reacting the product of the step (b) with trifluoromethanesulfonic acid anhydride in pyridine at a temperature of −50° C. to 50° C. to form the 3''-O-trifluoromethylsulfonyl derivative thereof, followed by allowing the latter derivative to stand in solution in pyridine at a temperature of 10° C. to 100° C. to produce tetra-$N^G$-acetyl-2,5,6-tri-O-acetyl-2'',3''-N,O-carbonyl-3''-epi-3',3'a;4'',6''-di-O-isopropylidene-dihydrostreptomycin of the formula

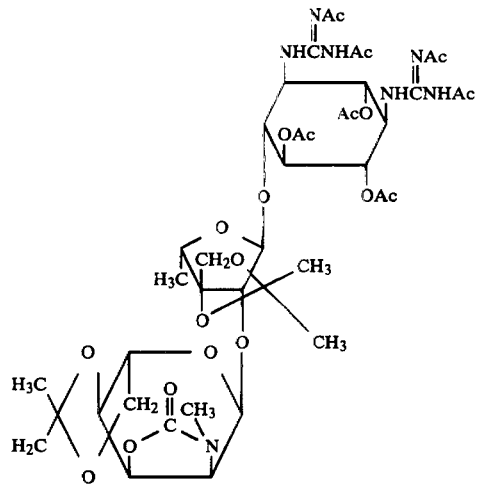

wherein Ac is as defined as above, (d) hydrolyzing the product of the step (c) with water in the presence of barium hydroxide with aqueous acetic acid to remove all the acetyl groups and the 2'',3''-N,O-carbonyl group therefrom and thus to produce 3''-epi-3',3'a;4'',6''-di-O-isopropylidene-dihydrostreptomycin, and (e) hydrolyzing the product of the step (d) to remove the 3',3'a;4'',6''-di-O-isopropylidene groups therefrom and thus to produce the desired 3''-epidihydrostreptomycin.

5. A process for the production of 3''-epidihydrostreptomycin, which comprises the consecutive steps of:

(a) reacting tetra-$N^G$-acetyl-2,5,6,3'a,3'',4'',6''-hepta-O-acetyl-dihydrostreptomycin of the formula

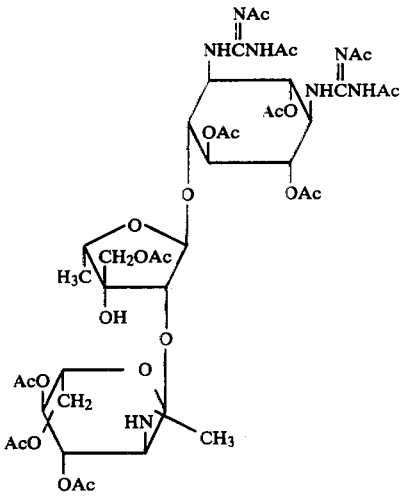

wherein Ac denotes an acetyl group, with ethanol at a temperature of 20°–30° C. to effect removal of the 3''-O-acetyl group from the above-mentioned N,O- acetylated dihydrostreptomycin compound and thereby to produce tetra-$N^G$-acetyl-2,5,6,3'a,4'',6'',6'''-hexa-O-acetyldihydrostreptomycin, (b) reacting the product of the step (a) with benzyloxycarbonyl chloride to produce tetra-$N^G$-acetyl-2,5,6,3'a,4'',6'''-hexa-O-acetyl-2''-N-benzyloxycarbonyldihydrostreptomycin, (c) reacting the product of the step (b) with methanesulfonyl chloride in pyridine to produce tetra-$N^G$-acetyl-2,5,6,3'a,4'',6'''-hexa-O-acetyl-2''-N-benzyloxycarbonyl -3''-O-methylsulfonyl-dihydrostreptomycin, (d) reacting the product of the step (c) either with 2-methoxyethanol at a temperature of 50° C. to 100° C. or with sodium methylate in methanol at a temperature of −20° C.~50° C., to produce 2'',3''-N,O-carbonyl-3''-epidihydrostreptomycin, and (e) hydrolyzing the product of the step (d) with water in the presence of barium hydroxide to remove the 2'',3''-N,O-carbonyl group therefrom and thus to produce the desired 3''-epidihydrostreptomycin.

6. A process for the production of 3''-epistreptomycin, which comprises the consecutive steps of:

(a) reacting 3''-epidihydrostreptomycin with a 1 molar or substantially 1 molar proportion of benzyloxycarbonyl chloride in a mixture of water and acetone at a temperature of −20° C. to 50° C. in the presence of an alkali metal carbonate to selectively benzyloxycarbonylate the 2''-methylamino group of 3''-epidihydrostreptomycin and thereby to produce 2''-benzyloxycarbonyl-3''-epidihydrostreptomycin, (b) reacting the product of the step (a) with 2,2-dimethoxypropane in the presence of p-toluene-sulfonic acid to produce 2''-N-benzyloxycarbonyl-3''-epi 3',3'a-O-isopropylidene-dihydrostreptomycin, (c) reacting the product of the step (b) with acetic anhydride in the presence of sodium acetate to produce tetra-$N^G$-acetyl-2,5,6,3'',4'',6'''-hexa-O-acetyl-2''-N-benzyloxycarbonyl-3''-epi-3',3'a-O-isopropylidene-dihydrostreptomycin, (d) hydrolyzing the product of the step (c) with aqueous acetic acid to produce tetra-$N^G$-acetyl-2,5,6,3'',4'',6'''-hexa-O-acetyl-2''-N-benzyloxycarbonyl-3''-epidihydrostreptomycin, (e) oxidizing the 3'-hydroxymethyl group of the product of the step (d) by reacting the latter compound with dimethylsulfoxide in the presence of pyridine, trifluoroacetic acid and dicyclohexylcarbodiimide to produce tetra-$N^G$-acetyl-2,5,6,3'',4'',6'''-hexa-O-acetyl-2''-N-benzyloxycarbonyl-3''-epistreptomycin, (f) removing all the acetyl groups from the product of the step (e) by hydrolysis with aqueous ammonia to produce 2''-N-benzyloxycarbonyl-3''-epistreptomycin, and (g) subjecting the 2''-N-benzyloxycarbonyl-3''-epistreptomycin to a catalytic hydrogenolysis with hydrogen to remove the 2''-N-benzyloxycarbonyl group therefrom and thus to produce the desired 3''-epistreptomycin.

7. An antibacterial composition comprising an antibacterially effective amount of 3''-epistreptomycin or 3''-epidihydrostreptomycin as the active ingredient, in combination with a pharmaceutically acceptable carrier for the active ingredient.

8. Tetra-$N^G$-acetyl-2,5,6-tri-O-acetyl-2'',3''-N,O-carbonyl -3''-epi-3',3'a;4'',6''-di-O-isopropylidene dihydrostreptomycin.

9. Tetra-$N^G$-acetyl-2,5,6,3'',4'',6'''-hexa-O-acetyl-2'',3''-N,O-carbonyl-3''-epidihydrostreptomycin.

10. Tetra-$N^G$-acetyl-2,5,6,3'',4'',6''',-hexa-O-acetyl-2''-N-benzyloxycarbonyl-3''-epistreptomycin.

* * * * *